(12) United States Patent
Nam et al.

(10) Patent No.: US 8,338,183 B2
(45) Date of Patent: Dec. 25, 2012

(54) ELECTROCHEMICAL DETERMINATION SYSTEM OF GLYCATED PROTEINS

(75) Inventors: Hakhyun Nam, Seoul (KR); Fenghua Zhang, Seoul (KR); Soon Hye Yang, Seoul (KR); Bo Kyeong Kang, Seoul (KR); Gang Cui, Seoul (KR); Moon Hee Choi, Kyonggi (KR); Joung Su Lee, Seoul (KR); Geun Sig Cha, Seoul (KR)

(73) Assignee: i-SENS, Inc., Seoul (KR)

(*) Notice: Subject to any disclaimer, the term of this patent is extended or adjusted under 35 U.S.C. 154(b) by 857 days.

(21) Appl. No.: 12/375,635

(22) PCT Filed: Jul. 29, 2006

(86) PCT No.: PCT/KR2006/002990
§ 371 (c)(1),
(2), (4) Date: Jan. 29, 2009

(87) PCT Pub. No.: WO2008/016193
PCT Pub. Date: Feb. 7, 2008

(65) Prior Publication Data
US 2009/0308744 A1    Dec. 17, 2009

(51) Int. Cl.
*G01N 33/50* (2006.01)
*G01N 33/48* (2006.01)

(52) U.S. Cl. .............. 436/67; 530/395; 205/778

(58) Field of Classification Search .......... 530/395–398, 530/412; 436/67, 518; 205/778
See application file for complete search history.

(56) References Cited

U.S. PATENT DOCUMENTS

| | | |
|---|---|---|
| 5,242,842 A | 9/1993 | Sundrehagen et al. |
| 5,541,117 A | 7/1996 | Karl et al. |
| 6,054,039 A | 4/2000 | Shieh |
| 6,162,645 A | 12/2000 | Lee et al. |
| 6,174,734 B1 | 1/2001 | Ito et al. |
| 6,562,581 B2 | 5/2003 | Law et al. |
| 6,677,158 B2 | 1/2004 | Hud et al. |
| 2003/0073243 A1 | 4/2003 | Law et al. |

FOREIGN PATENT DOCUMENTS

| | | |
|---|---|---|
| EP | 0194084 B1 | 9/1986 |
| EP | 0455225 B1 | 11/1991 |
| WO | WO-01/53831 A1 | 7/2001 |
| WO | WO-02/061436 A1 | 8/2002 |
| WO | WO-02/097416 A1 | 12/2002 |

*Primary Examiner* — J. Christopher Ball
(74) *Attorney, Agent, or Firm* — Nelson Mullins Riley & Scarborough LLP; EuiHoon Lee, Esq.; Pankaj Desai, Esq.

(57) ABSTRACT

Disclosed relates to an electrochemical determination system of glycated proteins, the system comprising: a filtering means for filtering labeled compounds bound to glycated proteins and non-glycated proteins after adding labeling compounds, capable of selectively binding to the glycated proteins to a solution, in which glycated/non-glycated proteins coexist, to be bound all to the glycated proteins; and a quantifying means for quantifying the filtered labeling compounds, not bound to the glycated proteins. The system of the present invention filters the residual labeled compounds left after binding to glycated proteins to quantify, instead of directly quantifying glycated proteins via the known glycated protein determination methods, thus simplifying the configuration of the system that can provide exact determinations with a low cost. Moreover, the electrochemical determination system of glycated proteins of the present invention minimizes the interference that the proteins are absorbed to an analysis device and a sensor in the system, not using immune antibodies that are expensive and have limited lives and, furthermore, not modifying the electrodes of the electrode sensor with antibodies or enzymes, thus facilitating mass production, quality control and circulation of the products.

8 Claims, 12 Drawing Sheets

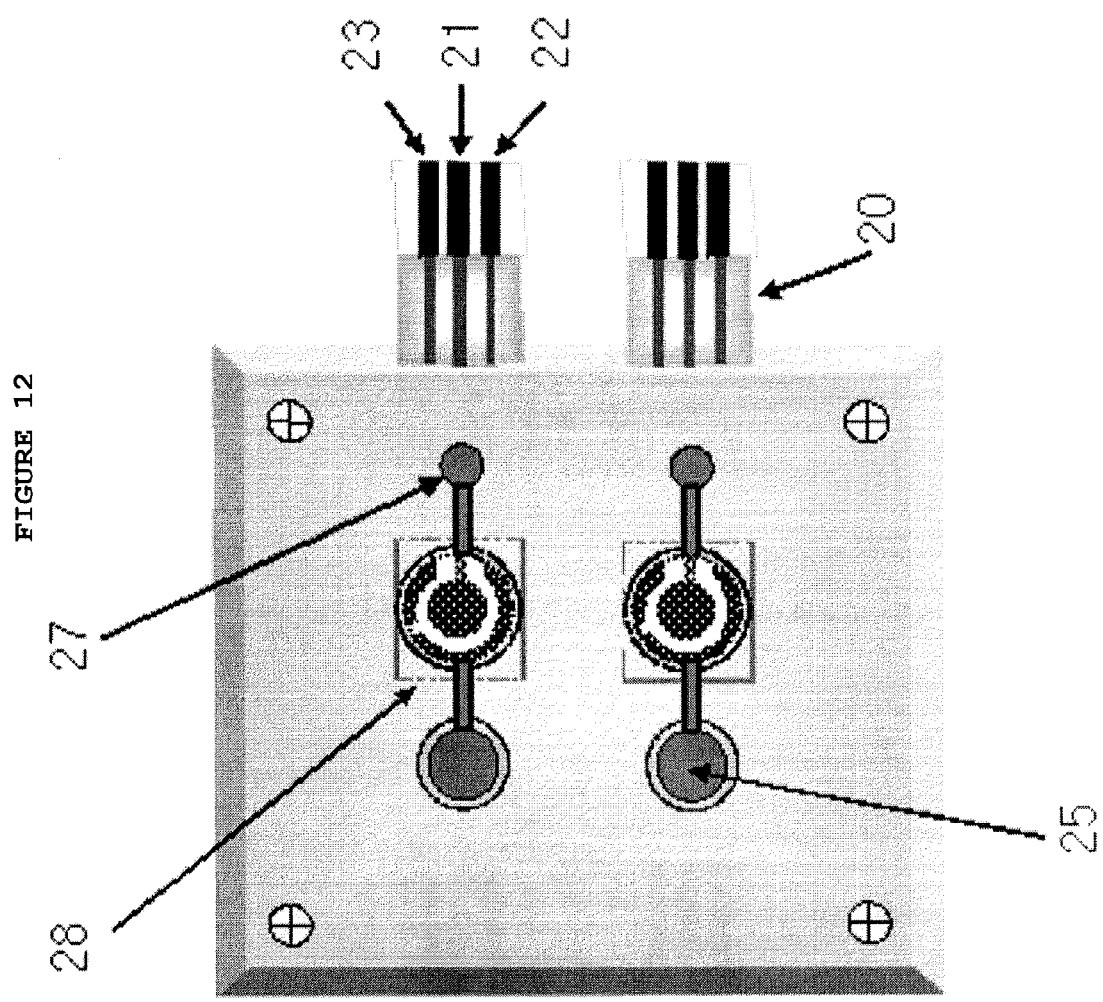

ELECTROCHEMICAL DETERMINATION SYSTEM OF GLYCATED PROTEINS

RELATED APPLICATIONS

This application is a 35 U.S.C. 371 national stage filing of International Application No. PCT/KR2006/002990filed on, Jul. 29, 2006, the contents of which are hereby incorporated by reference.

TECHNICAL FIELD

The present invention relates to an electrochemical determination system of glycated proteins and, more particularly, to a system comprising: a filtering means for filtering labeled compounds, bound to glycated proteins, and non-glycated proteins, after adding labeling compounds capable of selectively binding to the glycated proteins to a solution, in which glycated/non-glycated proteins coexist, to be bound all to the glycated proteins; and a quantifying means for quantifying the filtered labeling compounds, not bound to the glycated proteins.

BACKGROUND ART

Recently, a need for checking the amount of glucose in blood (blood glucose) periodically in diagnosing and preventing diabetes has been increased. Such blood glucose measurement may be carried out readily using a palm portable glucose meter and, more particularly, using a biosensor of test strip form for measuring blood glucose individually. However, since the blood glucose varies considerably according to the diet status and body status of a patient and the process of extracting blood necessary for the measurement is accompanied with pain, it is difficult for the patient to measure the blood glucose in conformity with its prescriptions exactly.

Glycated proteins, particularly, glycated hemoglobins are modified proteins produced through an Amadori rearrangement by reacting upon the glucose in blood for many hours. It has been well known that such glycated proteins are closely associated with an average level of blood glucose of a diabetic for two to three months. Accordingly, ordinary measurements of the blood glucose are important for the diabetic to confirm the daily health status and take necessary steps and, furthermore, the measurement of glycated proteins/hemoglobins is necessary to analyze the long term blood glucose and make an appropriate treatment, if necessary.

Standard measurement of glycated proteins is carried out in such a manner that the blood sample collected is mixed with an appropriate sample, e.g., a surfactant such as triton x-100, to be hemolyzed; the resulting sample is passed through a high performance liquid chromatography charged with boronic acid derivatives to be divided from normal proteins; and specific wavelengths of the proteins divided by visible rays are measured, thus calculating the glycation ratio. However, such standard measurement should be carried out by an expert using expensive chromatography equipment in a clinical laboratory well established. Accordingly, various researches aimed at developing method and apparatus for detecting the amount of glycated proteins readily to grasp the exact status of a diabetic in the field have continued to progress.

U.S. Pat. No. 5,541,117 has disclosed a method for determining glycated hemoglobin in blood comprising: treating a blood sample which contains the glycated hemoglobin to be hemolyzed; contacting the hemolyzed blood sample with a first immune reactant that specifically binds to glycated hemoglobin and a second immune reactant which binds to the first immune reactant; and determining binding of the first immune reactant to the second immune reactant as a determination of glycated hemoglobin in the blood sample. U.S. Pat. No. 6,677,158 has disclosed a method, similar to the former, for measurement of glycated hemoglobin by a rapid strip test procedure, in which boronic acid derivatives as a compound capable of coupling with glycated proteins selectively, instead of the immune reactants, are charged into a porous pad. Such immune chromatography method using the rapid test procedure can determine the ratio of glycated hemoglobin with ease, whereas, it has some drawbacks in that it should use expensive antibodies; it is difficult to manufacture the products having a regular quality due to the non-uniformity of the porous pad itself, used as a developing sheet; and its result is semi-quantitative.

Meanwhile, U.S. Pat. No. 5,242,842 has disclosed a method of assessing glycosylated hemoglobin in a sample containing both glycosylated and non-glycosylated hemoglobin in solution, in which the sample solution is contacted with signal-forming molecules to form a reaction mixture containing glycosylated hemoglobin having the signal-forming molecule; glycosylated hemoglobin having the signal-forming molecule is precipitated from the reaction mixture by a non-immobilized precipitating agent; and the precipitate is separated from the reaction mixture, thus assessing the signal-forming molecules which are bound to the separated hemoglobin and assessing the separated glycosylated and non-glycosylated hemoglobin. Such method provides an easy analysis using simplified portable equipment since the concentration of the signal-forming molecules bound to or separated with the hemoglobins may be determined from the strength of the signal obtained from the signal-forming molecules. U.S. Pat. No. 5,631,364 has disclosed labeled boronic acid derivatives useful for analyzing glycated proteins, in which an additional process for washing boronic acid derivatives, not bound to glycated proteins, is required and desired results can be obtained only when the exact amount of sample is applied to.

European Patent No. EP0194084 has disclosed a method an electrochemical assay for electrochemically assaying the mount of glycosylated proteins using ferrocene boronic acid or its derivative as a mediator for a wide range of oxidoreductases. However, such method cannot be utilized practically, since it cannot completely exclude the influence of glucose contained in blood. U.S. Pat. No. 6,054,039 has disclosed a method of determining the concentration of glycoproteins and glycosylated hemoglobin, in which porous films impregnated with compounds that cause oxidation-reduction reactions with glycoproteins are laminated to a sensing electrode having a mediator and a reference electrode is arranged faced with the sensing electrode. However, according to the method, the arrangement of the electrode sensors is complicated and it is difficult to estimate the relative amount of glycoproteins.

In addition, several methods applicable to the portable measurement instrument of glycated proteins have been disclosed in European Patent No. EP0455225, U.S. Pat. Nos. 6,174,734 and 6,162,645. Such methods are for determining the relative amount of glycated proteins by using enzyme-antibody conjugates or boronic acid derivative labeling compounds after separating proteins in a sample using a solid phase to which immune antibodies that couple with both glycated proteins and non-glycated proteins are immobilized. Furthermore, U.S. patent application Ser. No. 20030073243 has disclosed a method for quantitative determination of glycated hemoglobin, in which glycated hemoglobins are separated from non-glycated hemoglobins to determine the amount of glycated hemoglobins coupled with a solid phase surface via coloring method using catalytic properties of glycated hemoglobins for hydrogen peroxide.

The related arts cited above are all directed to a method of measuring glycated proteins spectroscopically or electrochemically by coupling markers with glycated proteins.

Accordingly, the inventors of the present invention have learned that it is possible to determine the amount of glycated proteins by measuring the amount of remaining markers separated after coupling with glycated proteins and completed the present invention.

DISCLOSURE OF INVENTION

Technical Problem

An object of the present invention is to provide an electrochemical determination system of glycated proteins that minimizes the influence on color and turbidity of a sample by proteins in a spectroscopic measurement and also minimizes the interference that the proteins are absorbed on the surface of electrodes in an electrochemical measurement.

In addition, the electrochemical determination system of glycated proteins in accordance with the present invention that filters residual markers can carry out the determination only with general electrodes, not with electrodes comprising enzymes and specific mediators.

Technical Solution

To accomplish the object of the present invention, there is provided an electrochemical determination system of glycated proteins comprising a filtering means for filtering labeled compounds, bound to glycated proteins, and non-glycated proteins, after adding labeling compounds capable of selectively binding to the glycated proteins to a solution, in which glycated/non-glycated proteins coexist, to be bound all to the glycated proteins; and a quantifying means for quantifying the filtered labeling compounds, not bound to the glycated proteins.

Advantageous Effects

An electrochemical determination system of glycated proteins in accordance with the present invention filters the residual labeled compounds left after binding to glycated proteins to quantify, instead of directly quantifying glycated proteins via the known glycated protein determination methods, thus simplifying the configuration of the system that can provide exact determinations with a low cost. Another advantageous effect of the electrochemical determination system of glycated proteins in accordance with the present invention is to minimize the interference that the proteins are absorbed to an analysis device and a sensor in the system, not using immune antibodies that are expensive and have limited lives and, furthermore, not modifying the electrodes of the electrode sensor with antibodies or enzymes, thus facilitating mass production, quality control and circulation of the products.

BRIEF DESCRIPTION OF THE DRAWINGS

FIG. 12 shows an example of a screen-printing type electrode sensor in accordance with another embodiment of the present invention.

BEST MODE FOR CARRYING OUT THE INVENTION

Figure 1:
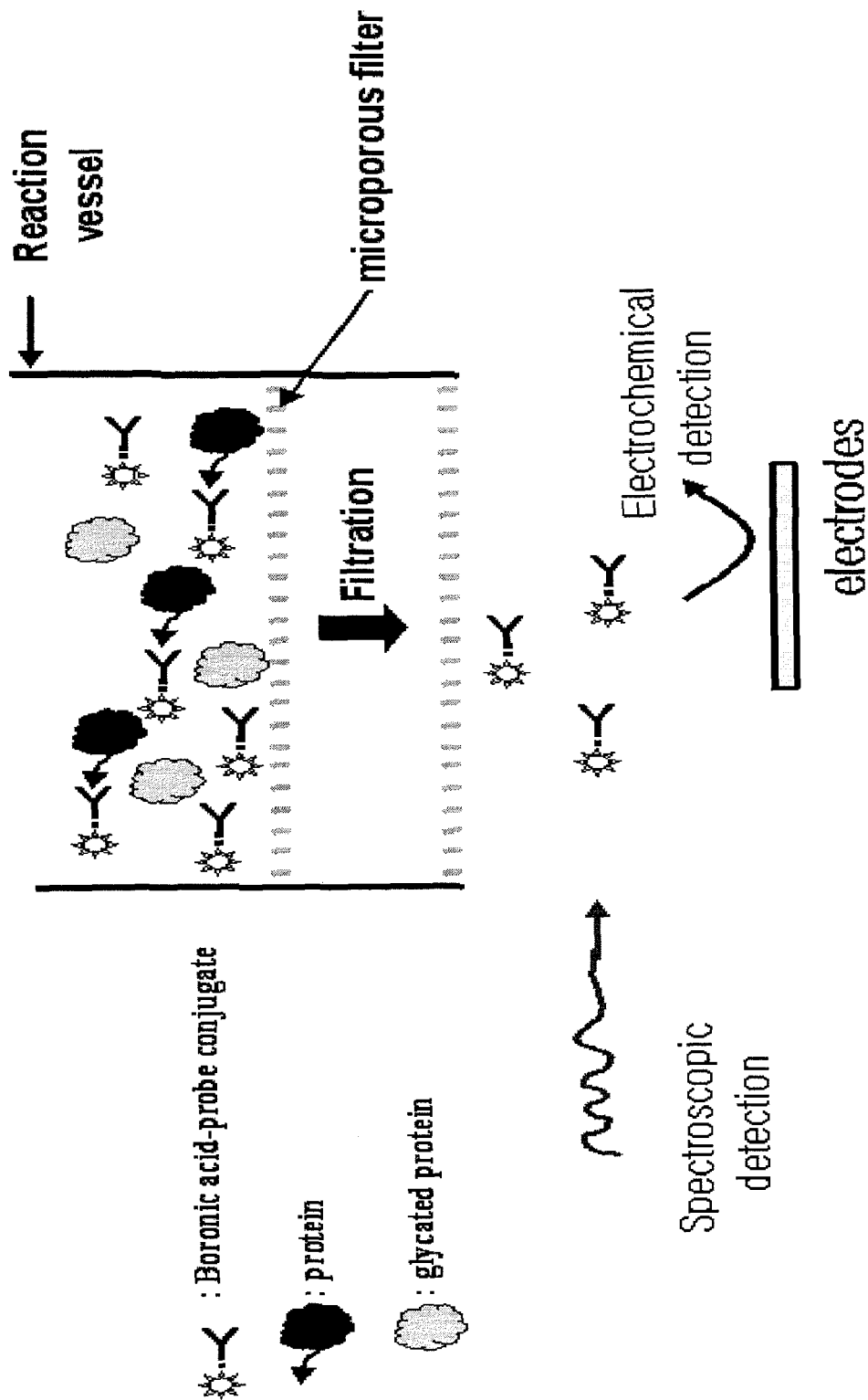
FIG. 1 is a conceptual diagram depicting an electrochemical determination system of glycated proteins in accordance with the present invention.

The present invention provides an electrochemical determination system of glycated proteins.

In the electrochemical determination system of glycated proteins of the present invention, the system comprises a filtering means for filtering labeled compounds, bound to glycated proteins, and non-glycated proteins, after adding labeling compounds having a relatively small molecular weight and capable of selectively binding to the glycated proteins to a sample solution, in which glycated/non-glycated proteins coexist, to be bound to the glycated proteins. Glycated proteins having a large molecular weight and the other interference species are separated from the labeled compound of small molecular weight and filtered by the filtering means. The labeled compounds contained in the filtered sample are determined by an analyzer or a sensor, which can recognize the labeled compounds and is generally used in the field related to the present invention, thus measuring the amount of glycated proteins existing.

In the electrochemical determination system of glycated proteins, any labeling compounds may be used without limitations if the compounds are prepared with boronic acid derivatives, for which an electrochemical oxidation-reduction pair functional group, a spectroscopic chromophoric group, a substrate functional group of enzyme, etc. is substituted, desirably, it may use ferrocene derivatives, anthraquinone and its derivatives, organic conductive salt, etc. as the labeling compounds and, preferably, it may use boronic acid derivatives including a substituent having at least one compound selected from the group consisting of viologen, dimethylferrocene (DMF), ferricinium, ferrocene monocarboxylic acid (FCOOH), 7,7,8,8-tetracyanoquinodimethane (TCNQ), Pyrroloquinoline quinine (PQQ), tetrathiafulvalene (TTF), N-methyl acidinium (NMA+), tetrathiatetracene (TTT), N-methylphenazinium (NMP+), hydroquinone, 3-dimethylaminobenzoic acid (MBTH-DMAB), 3-methyl-2-benzothio-zolinone hydrazone, 2-methoxy-4-allylphenol, 4-aminoantipyrin (AAP), dimethylaniline, 4-aminoantipyrene, 4-methoxynaphthol, 3,3',5,5'-tetramethyl benzidine (TMB), 2,2-azino-di-[3-ethyl-benzthiazoline sulfonate], o-dianisidine, o-toluidine, 2,4-dichlorophenol, 4-amino phenazone and benzidine. Such boronic acid derivatives having the active substituent can cause a specific reaction with glycated proteins.

A preferred embodiment of the electrochemical determination system of glycated proteins in accordance with the present invention may be materialized preferably by an electrode sensor for determining glycated proteins.

The preferred embodiment of the electrode sensor for determining glycated proteins in accordance with the present invention comprises an electrode body including a working electrode and a counter electrode arranged symmetrically on both ends of a microporous film. Here, it is desirable that a protein removal filter is arranged in front of the working electrode spaced a predetermined distance apart and an absorption pad is established on the surface of the counter electrode in order for the sample containing the labeled compounds, in which proteins are removed, to flow smoothly in one direction. The absorption pad absorbs the sample added to one surface of the porous electrode to transfer the absorbed sample easily to the opposite side of the electrode. With the porous electrode having no sufficient hydrophile property, the sample transfer is not made uniformly, thus resulting in a serious error in the analysis. The absorption pad is to solve such problem. By means of the absorption pad, the protein-removed sample flows in one direction and the labeled compound contained the protein-removed sample are determined via a spectroscopical analyzing method or an electrochemical analyzing method. That is, it is possible to measure the amount of existing glycated proteins by coupling the electrode sensor of the invention with a device that can read current produced after applying voltage or pulse voltage to the electrode sensor for a predetermined period.

Another embodiment of the electrode sensor for determining glycated proteins in accordance with the present invention comprises: a sample inlet established on an insulation substrate; a protein removal filter provided in the sample inlet; an electrode body including a working electrode, a counter electrode and, selectively, a reference electrode mounted on one or two insulation substrates; and a capillary flow path or a microfluidic path arranged from the sample inlet to the electrode sensor, the upper plates of the insulation substrates being processed to have a hydrophile property, thus making the sample flow along with the flow path easily. Accordingly, the protein-removed sample flows in one direction and the labeled compounds contained the protein-removed sample are determined via an electrochemical analyzing method or a spectroscopical analyzing method. That is, it is possible to measure the amount of existing glycated proteins by coupling the electrode sensor of the invention to a device that can read currents produced after applying voltage or pulse voltage to the electrode sensor for a predetermined period.

The amount of glycated proteins is determined from a difference between the total concentration of the labeled compounds and the detected concentration of the labeled compounds.

The electrochemical determination system of glycated proteins of the present invention may further comprises a means for determining a relative amount between non-glycated proteins and glycated proteins. The relative amount between non-glycated proteins and glycated proteins can be determined by measuring the labeled compounds contained in the protein-removed sample via an electrochemical method or a spectroscopical determination method. Here, the amount of the labeled compounds contained in the protein-removed sample may be determined by measuring the absorbency, or the amount of fluorescence, phosphorescence or chemiluminescence.

Figure 8:
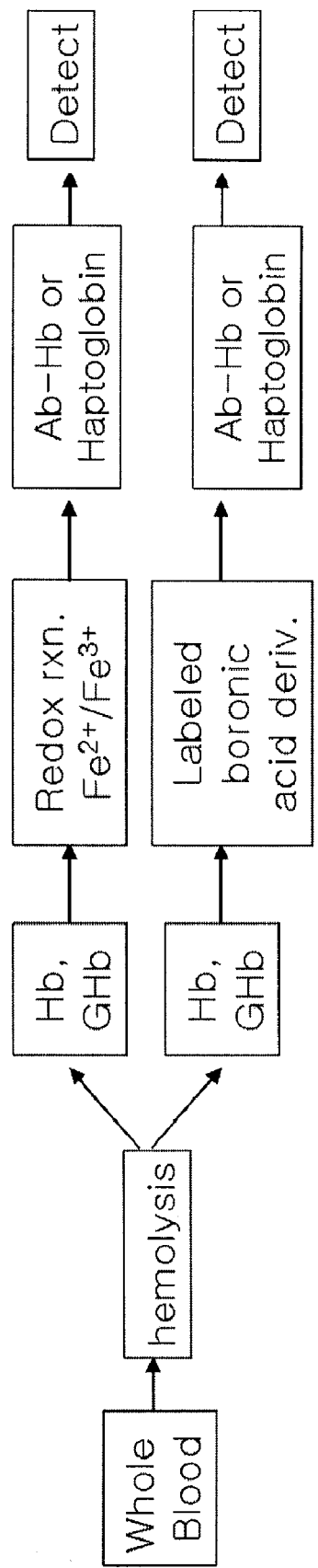
FIG. 8 is a conceptual diagram illustrating a microfluidic determination system of glycated proteins that materializes the present invention.

It is desirable that such means is designed to make the sample mixed with non-glycated proteins and glycated proteins flow through two individual microfluidic paths, as depicted in FIG. 8, in which the inside of one flow path includes a means for filtrating glycated proteins by establishing a modified surface after chemically or physically immobilizing labeling compounds, preferably, boronic acid derivatives with a substituent or a labeled compound immobilized insert, preferably, a boronic acid derivative immobilized insert that makes the liquid sample flow continuously; and a means for determining a relative amount between non-glycated proteins and glycated proteins via an electrochemical method or a spectroscopical method, provided at the end of the flow path, and the other flow path includes iron cyanides (II)/(III) that cause a direct oxidation-reduction reaction with glycated hemoglobins (GHb) to be detected electrochemically, thus determining the total amount of glycated/non-glycated hemoglobins. The microfluidic determination system of glycated proteins has an advantage in that the amount of glycated hemoglobins can be measured without a specific separation process for the total amount of glycated/non-glycated hemoglobins.

Moreover, it is desirable that such means is designed to make the sample mixed with non-glycated proteins and glycated proteins flow through two individual microfluidic paths, in which the labeling compounds bound to non-glycated proteins flows through one flow path continuously and the labeling compounds bound to glycated proteins flows through the other flow path continuously, the insides of both flow paths including a means for filtrating glycated proteins and non-glycated proteins as well by establishing a modified surface after chemically or physically immobilizing immune antibodies capable of a specific binding to the proteins for analysis or an insert, having immune antibodies, which makes the liquid sample flow continuously; and a means for determining a relative amount between glycated proteins and non-glycated proteins via an electrochemical method or a spectroscopical method, in which only the labeled compounds flow to the end of the microfluidic path.

In addition, the present invention further comprises a sample-pretreatment dispenser suitable for the electrochemical determination system of glycated proteins of the present invention.

The sample-pretreatment dispenser desirably comprises a capillary tube for sample extraction; a sample injection plunger having a capillary tube insertion hole for inserting the extracted sample; and a vessel of injector type, in which the sample injection plunger is mounted on an end thereof and a sample dispensing hole for dispensing the sample is formed on the other end.

The sample-pretreatment may be carried out desirably by mixing the injected sample with hemolytic and labeling compounds in the vessel of injector type of the sample-pretreatment dispenser.

The sample-pretreatment dispenser may further comprises a protein removal filter layer additionally, which substitutes for a filter mounted in a sensor to play the same role, thus simplifying the configuration of the sensor and providing an advantage of mass production.

Mode for the Invention

Hereinafter, the present invention will now be described more fully with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

FIG. 1 is a conceptual diagram depicting an electrochemical determination system of glycated proteins in accordance with the present invention, in which the measurement is carried out comprising adding boronic acid derivatives to a solution, in which glycated and non-glycated proteins coexists, to be bound all to the glycated proteins; removing proteins having large molecular weights; and subtracting the detected concentration of boronic acid derivatives from the total concentration of boronic acid derivatives using an appropriate method for determining the boronic acid derivatives, i.e., using a spectroscopical method or an electrochemical method, thus measuring the amount of glycated proteins.

Figure 2:
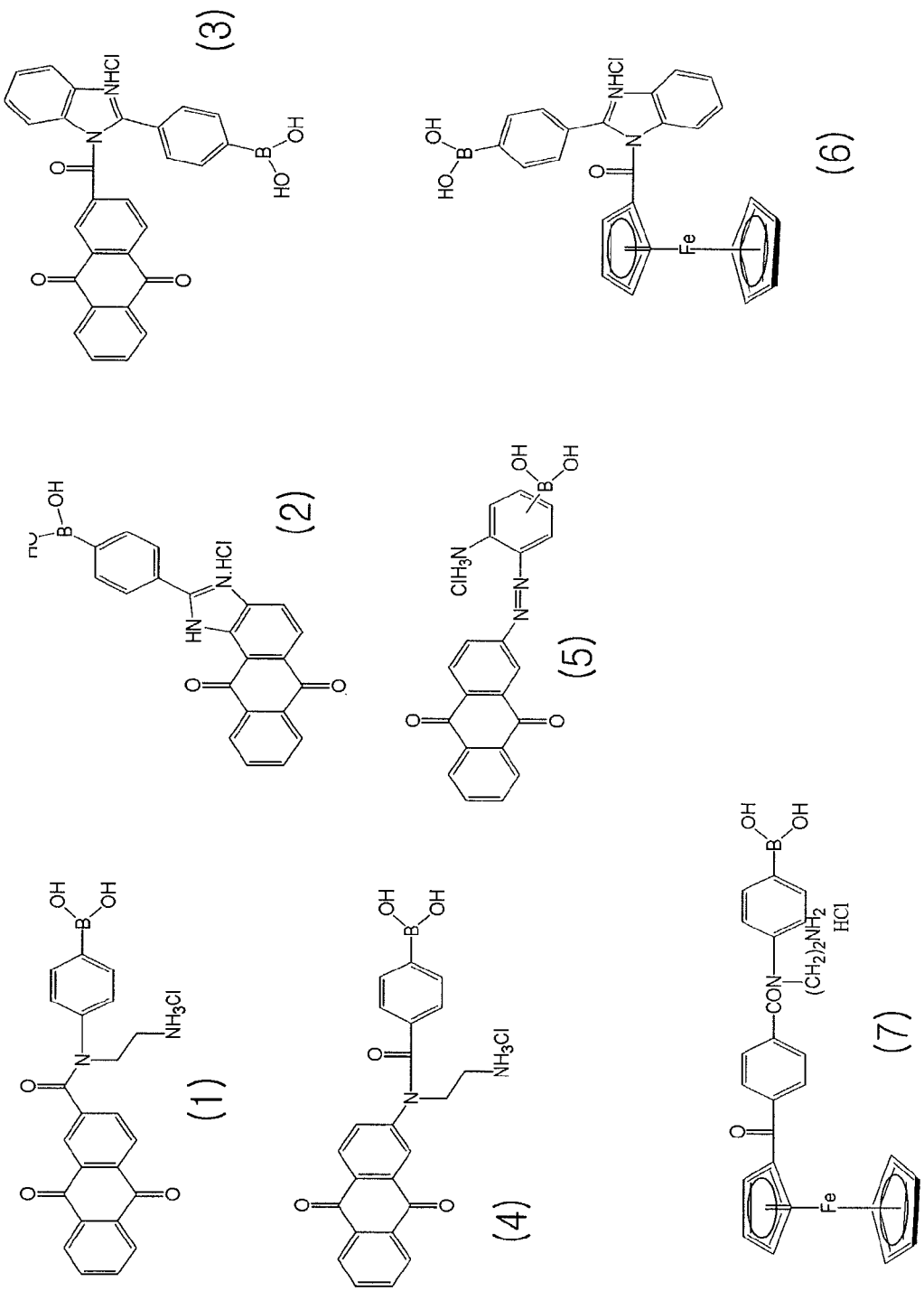
FIG. 2 shows examples of derivatives suitable for the determination of glycated proteins in accordance with the present invention.

FIG. 2 shows examples of boronic acid derivatives suitable for the determination of glycated proteins, for which electrochemical activating groups are substituted. Particularly, chemical formula (1) denotes 4-[2-aminoethyl-(2-anthra-5,10-dioxo-carbonyl)amino]-phenyl boronic acid monohydrochloride; formula (2) denotes 4-[11H-anthra{1,2-d}imidazole-5,10-dioxo]-phenyl boronic acid monohydrochloride; formula (3) denotes 4-[N-{anthraquinone-1-carbonyl}-benzoimidazole]-phenyl boronic acid monohydrochloride; formula (4) denotes 4-[2-aminoethyl-(2-anthra-5,10-dioxo-amino)carbonyl]-phenyl boronic acid monohydrochloride; formula (5) 3-amino-4-[2-anthra-5,10-dioxo-azo]phenyl boronic acid monohydrochloride; formula (6) denotes 4-[2-{N-ferrocenoyl-benzoimidazole}]-phenyl boronic acid monohydrochloride; and formula (7) denotes 4-[N,N-2-aminoethyl-{4-ferrocenoylbenzoyl}-amino]-phenyl boronic acid monohydrochloride, respectively.

Figure 3:
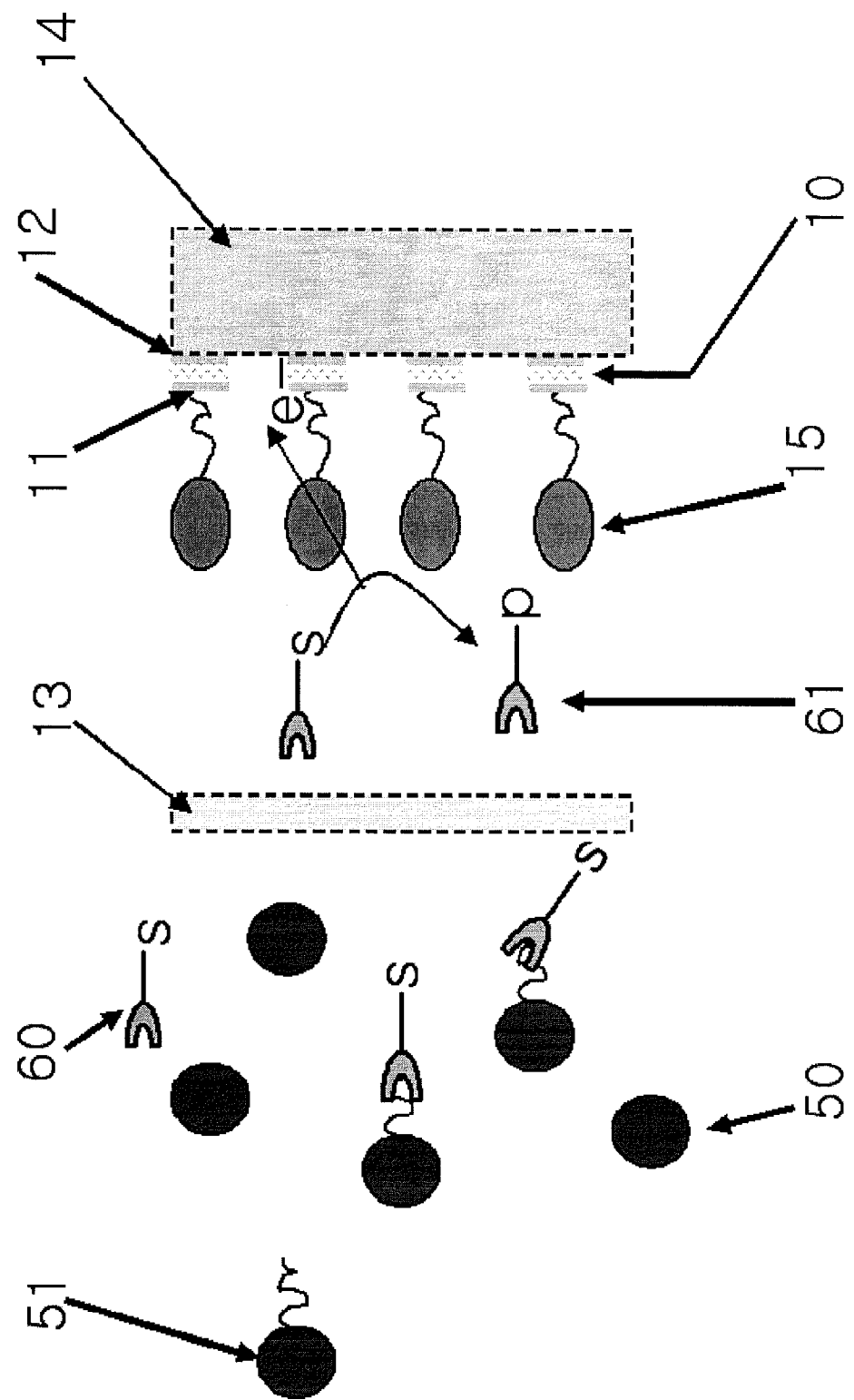
FIGS. 3 and 4 depict examples of electrochemical determination system of glycated proteins in accordance with a preferred embodiment of the present invention.
Figure 4:
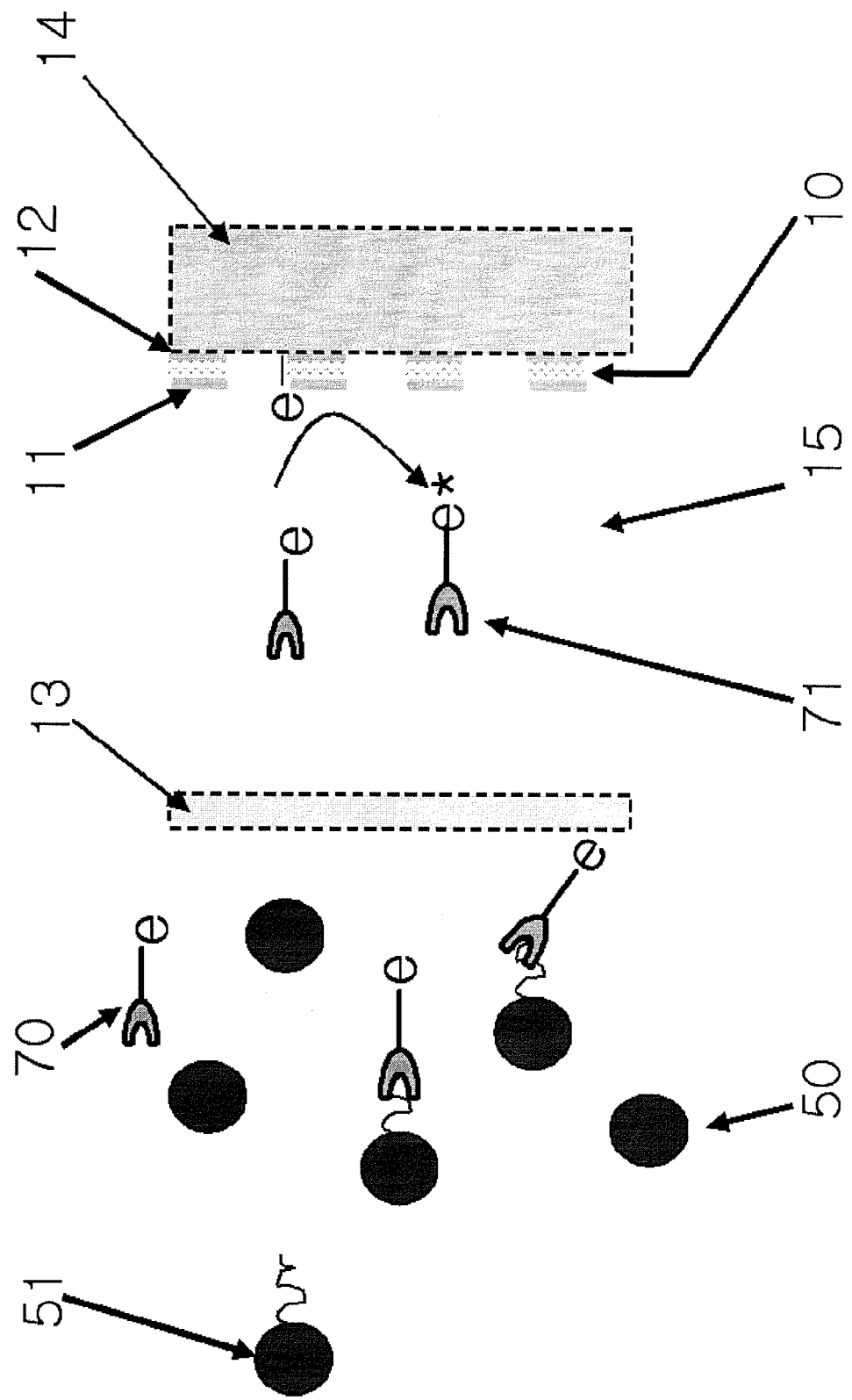
Figure 5:
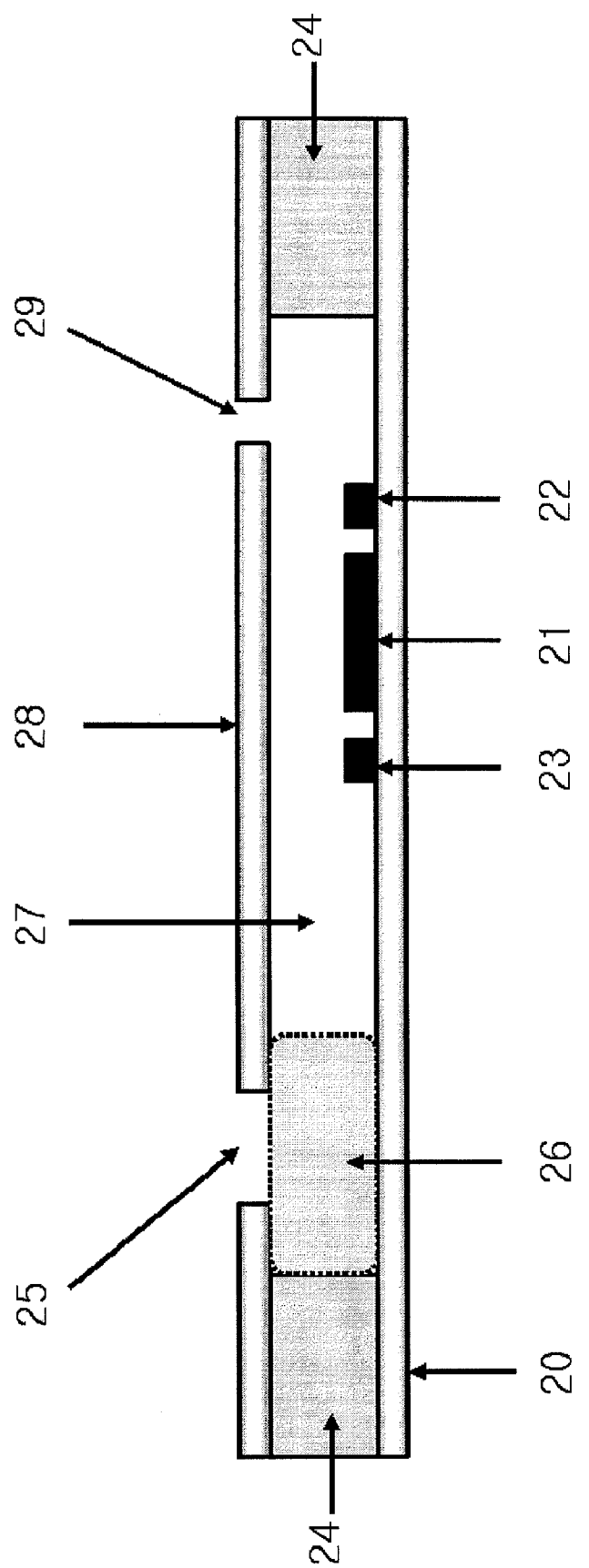
FIG. 5 depicts an example of a glycated protein determination sensor in accordance with another preferred embodiment of the present invention.

FIGS. 3 and 4 depict examples of electrochemical determination system of glycated proteins in accordance with a preferred embodiment of the present invention, in which the systems are designed to configure a working electrode 11 and a counter electrode 12 faced with each other on the front and back sides of a porous film 10, preferably, a nylon or cellulose film having pores of micrometer sizes, via a plasma chemical vapor deposition process or a metal paste and provide a protein removal filter 13 in front of the working electrode 11 and an absorption pad 14 in front of the counter electrode 12 to make the sample containing protein-removed boronic acid derivative markers flow in one direction. When the substrate of the boronic acid derivative markers to be used is enzyme, the surface of the working electrode 11 is modified to enzymes 15 corresponding to the markers to determine the amount of markers, as shown in FIGS. 3 and 4; and when the markers are general electrochemical ones, the surface of the working electrode is not modified but used as it is, as shown in FIGS. 6 and 7.

Figure 6:
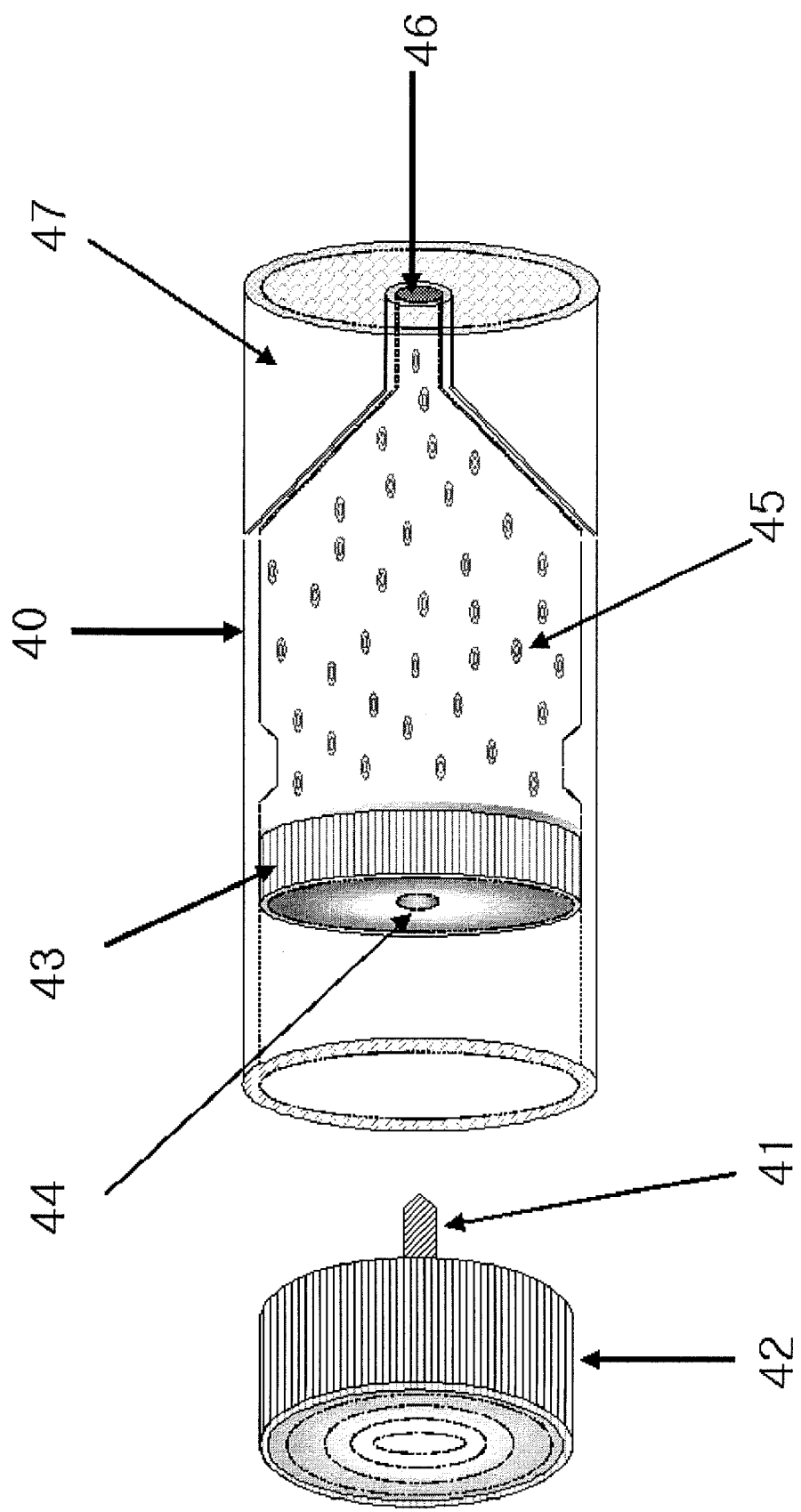
FIGS. 6 and 7 show examples of sample-pretreatment dispensers suitable for the electrochemical determination system of glycated proteins in accordance with other embodiments of the present invention.
Figure 7:
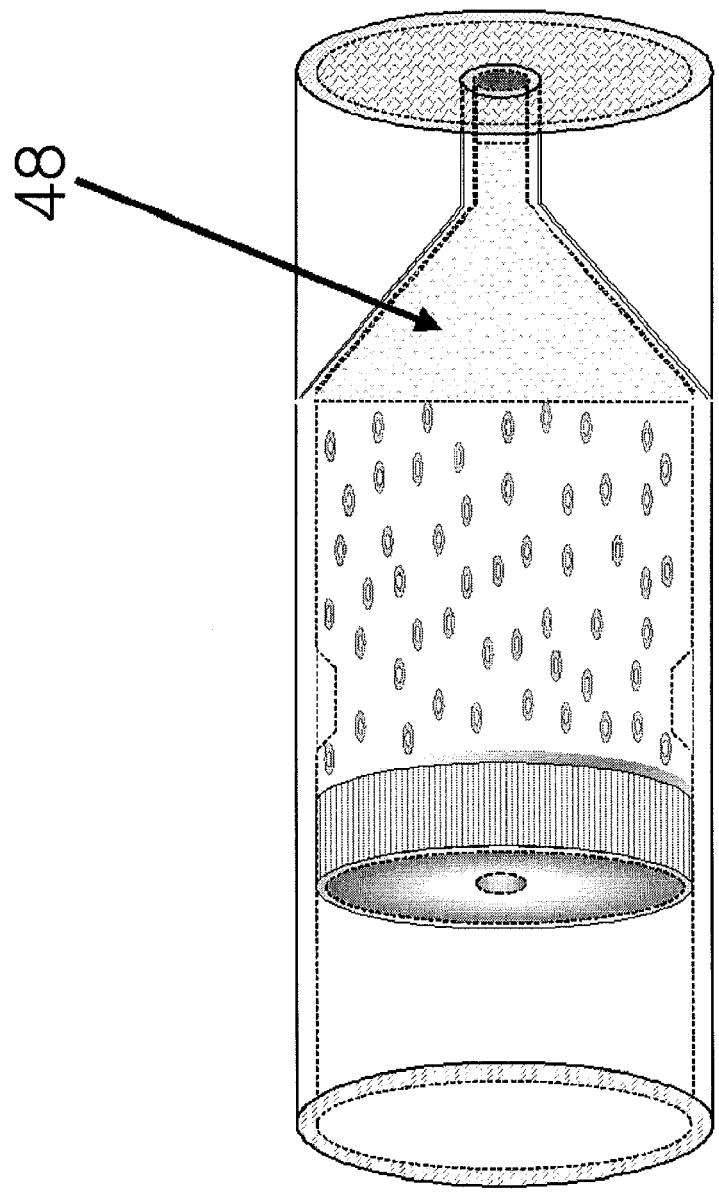
Figure 7:
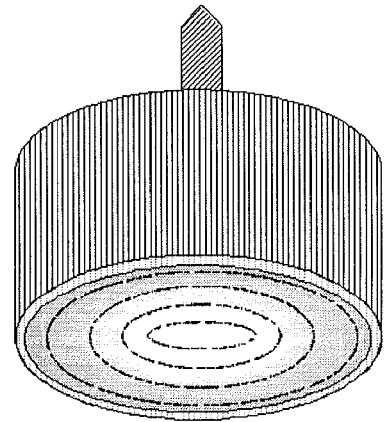

FIGS. 6 and 7 depict an example of a glycated protein determination sensor in accordance with another preferred embodiment of the present invention, in which a working electrode 21, a counter electrode 22 and a reference electrode 23 are formed on an insulation substrate 20 made of plastic, silicon or ceramic via a method such as vacuum evaporation, screen-printing or photolithography process. Further, the glycated protein determination sensor comprises adhesive layers 24 of double-sided tape or of a predetermined thickness having a flow path for leading the flow of the sample on the electrode substrate, a protein removal pad 26 contacting with a sample injection hole 25 and an upper plate 28 treated with an appropriate hydrophilic process in order for the injected sample to flow easily along with a capillary tube flow path 27, thus materializing the concept of the present invention proposed in FIG. 1.

In case where the relative ratio of glycated proteins for the total amount of proteins is more important than the absolute amount of glycated proteins, an electrode for measuring the amount of non-glycated proteins or the total amount of proteins may be used at the same time. Typically, in case of glycated hemoglobins, after reacting glycated hemoglobins with a reagent containing ferricyanides ($Fe^{3+}$) that cause oxidation-reduction reactions with hemoglobins or with a sample layer, in which such reagent is immobilized, prior to the filter 13 or the pad 26, the resulting sample is passed through the protein removal filter 26 to measure the amount of reduced $Fe^{2+}$, thus determining the total amount of hemoglobins. The determination of $Fe^{2+}/Fe^{3+}$ contained in the filtrated sample can be carried out exactly using a double pulse of oxidation and reduction.

FIG. 8 depicts one of the major elements of the electrochemical determination system of glycated proteins in accordance with other embodiments of the present invention, in which an example of a sample-pretreatment dispenser 40 exactly adopts a necessary amount of a liquid sample extracted from a living body to take an appropriate pretreatment and couple the pretreated sample with labeling compounds. After extracting the sample from the living body via a capillary tube 41, a capillary tube cap 42 is inserted into a sample injection hole 44 provided in a plunger 43 and the dispenser 40 is shaken to mix the sample injected with hemolytic and labeling compounds 45 filled in advance. After a lapse of sufficient reaction time, a sample outlet cap 47 is opened to make the sample get out of the dispenser 40 through a sample outlet 46 by pushing the plunger 43 coupled with the capillary tube cap 42, thus injecting the appropriate amount of sample to an electrode sensor or a spectroscopic cell prepared. The sample-pretreatment dispenser 40 of the present invention has an advantage in that it can take an appropriate pretreatment of sample and then inject the resulting sample to a measurement sensor without using a separate pipette or a vessel.

Figure 9:
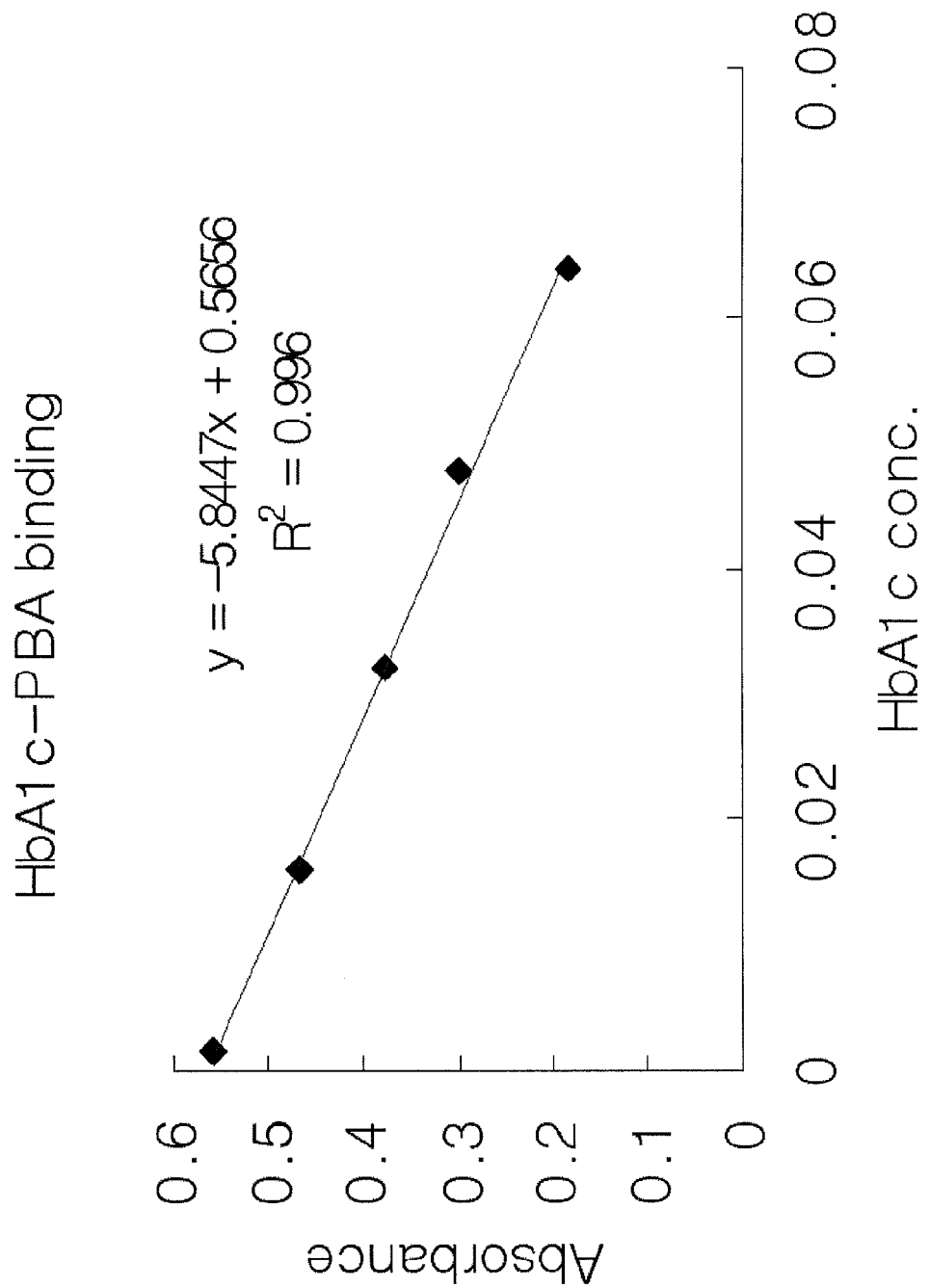
FIG. 9 is a graph showing spectroscopic results of glycated proteins determined in accordance with another embodiment of the present invention.
Figure 10:
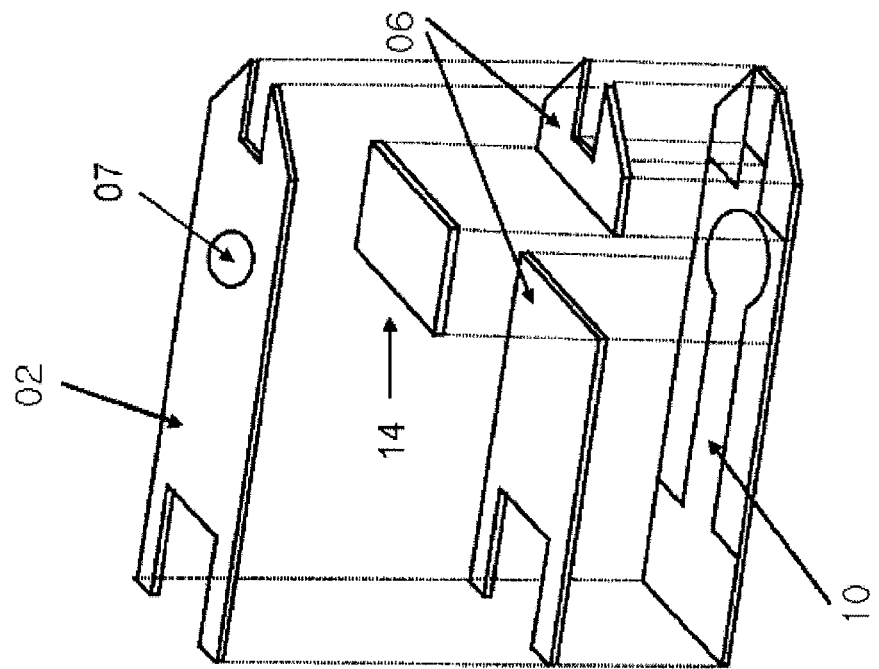
FIG. 10 shows an example of an electrode sensor in accordance with another embodiment of the present invention.
Figure 10:
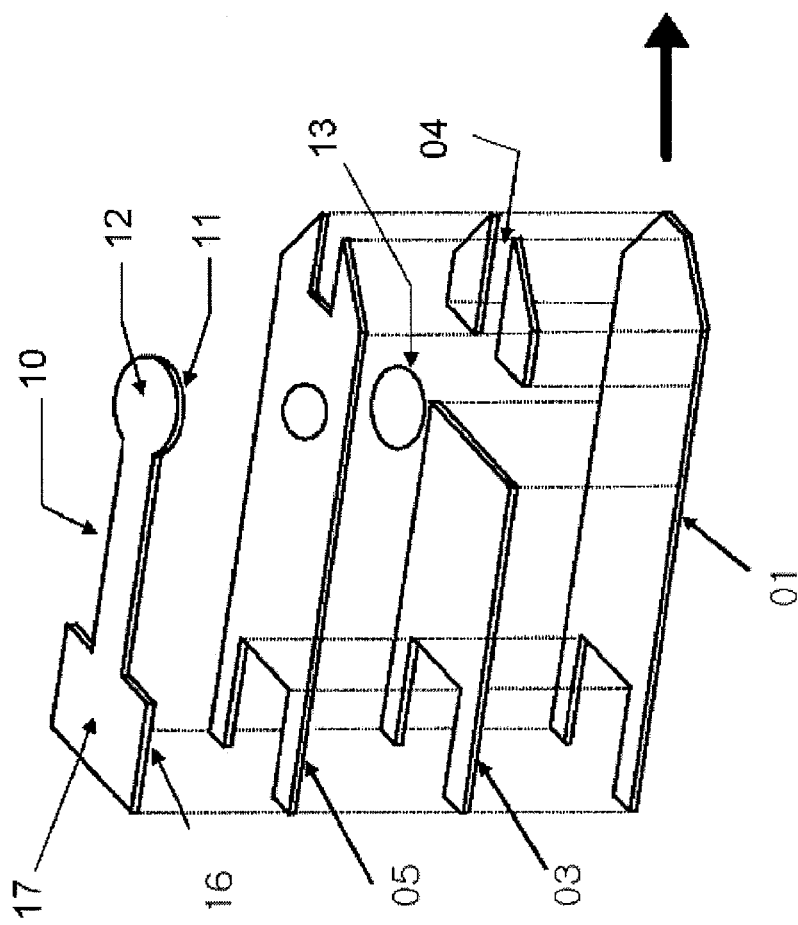

FIG. 9 depicts another example of the sample-pretreatment dispenser of the present invention, in which a protein removal filter 48 is established in the region of the sample outlet to play the same role of the filter 13 or the pad 26. In this case, the configuration of the glycated protein determination sensor can by simplified to facilitate the mass production of the sensor.

FIG. 8 is a flow diagram showing the overall process of the present invention materialized with a microfluidic lab-on-a-chip, in which the microfluidic chip uses immune antibodies capable of a specific binding to the proteins for analysis instead of the protein removal filter to remove glycated/non-glycated proteins, thus detecting the markers only.

Next, the present invention will now be described in more detail with preferred examples.

EXAMPLE 1

0.16 mM of hemolyzed HbA1c arranged by mixing 200 μ of 10% HbA1c control standard solution supplied by Bio-Rad Laboratories with 800 μ of hemolytic was mixed with 500 μ of phosphate buffer of pH 10.5 to arrange samples of 0.128, 0.096, 0.064, 0.032 and 0.0032 mM of 500 μ each. Then, the samples were mixed with p-phenylboronic amine (PBA) dissolved in 500 μ of the same buffer and left them for ten minutes. Subsequently, the samples were put into Ultra-4 Centrifugal Filter Device manufactured by Amicon Inc. to separate hemoglobin proteins. Next, UV absorbency of PBA contained in the separated solutions was obtained in quartz cells and absorbency of PBA corresponding to the respective concentrations of HbA1c was measured at 240 nm.

FIG. 9 depicts the results of measurement, from which it can be understood that the absorbency of PBA contained in the separated solution is decreased as much as the concentration of HbA1c is increased.

EXAMPLE 2

An electrode sensor suitable for materializing the concept of the present invention was configured as depicted in FIG. 8. First, a tape 03 having a sample injection path 04 was laminated on a lower substrate 01 of polyethylene (PET), a cellulose film or a nylon film 13 for removing hemocytes and proteins was put thereon and a middle substrate 05 were arranged to fix the film 13. An electrode body 10 including a working electrode 11 and a counter electrode 12 formed with nylon deposited with aurum via vacuum evaporation was put thereon and a middle substrate 06 of double-sided tape fixed the electrode body 10. An absorption pad 14 was fixed on the counter electrode 12 and an upper substrate 02 of PET was provided finally to protect the whole electrode sensor. A sample obtained using ferrocene boronic acid derivative markers of FIG. 2 via the method proposed in Example 1 was injected to the electrode sensor configured as described above and a voltage of +400 mV was applied thereto to measure currents. As a result, it was learned that current signals were decreased as much as the amount of HbA1c was increased.

EXAMPLE 3

Figure 11:
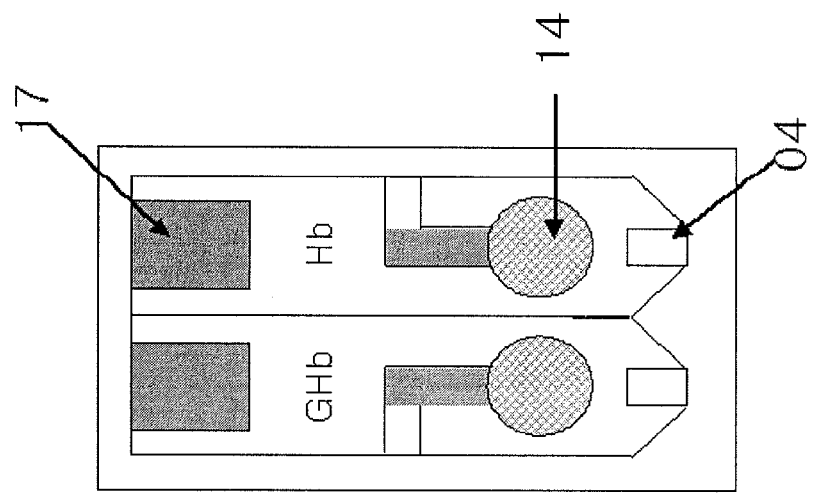
FIG. 11 shows an example of the electrode sensor assembly and a monitor in accordance with another embodiment of the present invention.
Figure 11:
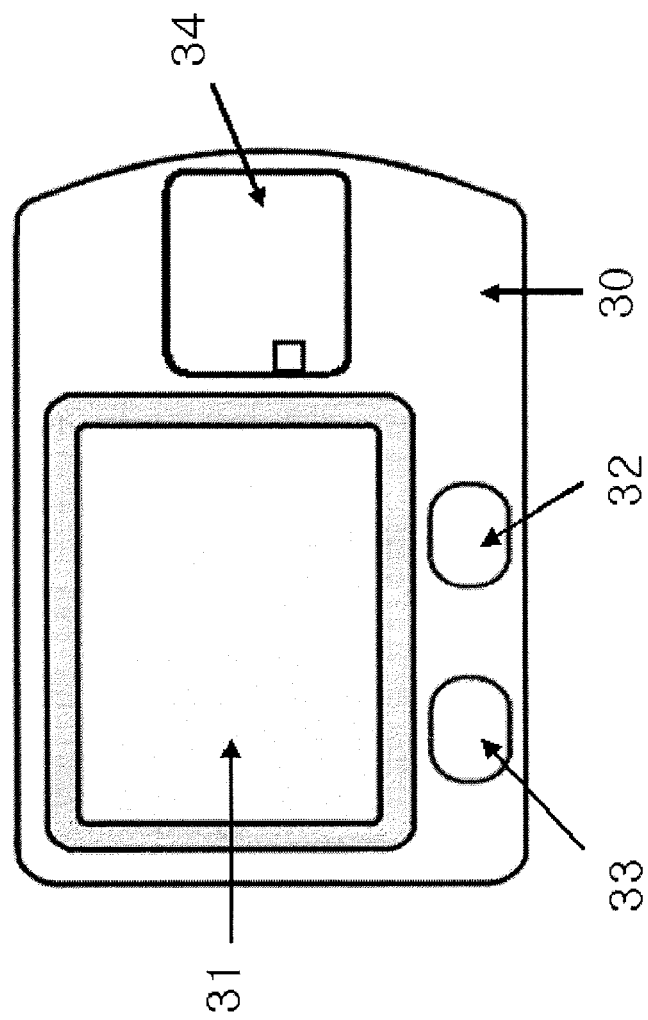

The electrode sensors materialized in the manner of Example 2 were coupled in parallel with each other to configure an electrode sensor assembly as shown in FIG. 11. A sample arranged in the same manner as Example 2 was injected to one electrode sensor and a sample processed with ferricyanides was injected to the other electrode sensor. Then, a voltage of +400 mV was applied thereto to measure currents, thus obtaining signals in proportion to the total amount of hemoglobin. From the ratio of the current signals obtained from the two electrode bodies, abundance ratio of glycated hemoglobin was calculated using the electrode sensor assembly depicted in FIG. 11.

EXAMPLE 4

Electrodes were formed via screen-printing on PET film and the electrode assemblies were coupled in parallel with each other as shown in FIG. 12, in which a ventilation (28) is provided for facilitating the injection of sample through a sample injection hole 25. A sample arranged in the same manner as Example 2 was injected to one electrode sensor and a sample processed with ferricyanides was injected to the other electrode sensor. Then, a voltage of +400 mV was applied thereto to measure currents, thus obtaining signals in proportion to the total amount of hemoglobin. From the ratio of the current signals obtained from the two electrode bodies, abundance ratio of glycated hemoglobin was calculated and the results well corresponded to those obtained by standard equipment of Bio-Rad Laboratories.

Although the present invention has been described with reference to certain exemplary embodiments thereof, it will be understood by those skilled in the art that a variety of modifications may be made therein without departing from the spirit or scope of the present invention defined by the appended claims and their equivalents.

The invention claimed is:

1. A method of measuring glycated proteins in a solution in which glycated/non-glycated proteins coexist comprising:
    adding labeling compounds capable of selectively binding to the glycated proteins, to a solution in which glycated/non-glycated proteins coexist;
    wherein the labeling compound is a boronic acid derivative including a substituent having at least one compound selected from the group consisting of viologen, dimethylferrocene (DMF), ferricinium, ferrocene monocarboxylic acid (FCOOH), 7,7,8,8-tetracyanoquinodimethane (TCNQ), pyrroloquinoline quinine (PQQ), tetrathiafulvalene (TTF), N-methyl acidinium (NMA+), tetrathiatetracene (TTT), N-methylphenazinium (NMP+), hydroquinone, 3-dimethylaminobenzoic acid (MBTHDMAB), 3-methy1-2-benzothio-zolinone hydrazone, 2-methoxy-4-allylphenol, 4-aminoantipyrin (AAP), dimethylaniline, 4-aminoantipyrene, 4-methoxynaphthol, 3,3',5,5'tetramethyl benzidine (TMB), 2,2-azino-di-[3-ethyl-benzthiazoline sulfonate], o-dianisidine, o-toluidine, 2,4-dichlorophenol, 4-amino phenazone and benzidine,
    filtering the solution to which labeling compounds are added, to remove glycated proteins bound to labeling compounds and non-glycated proteins from the solution through a filtering means; and
    quantifying by electrochemical determination, the residual labeling compounds, not bound to the glycated proteins in the filtered solution passing through the filtering means;
    wherein the amount of glycated proteins is determined from a difference between an added concentration of the labeling compounds in adding step and a quantified concentration of the labeling compounds in quantifying step.

2. The method of measuring glycated proteins as recited in claim 1,
    wherein further comprises determining a relative amount between non-glycated proteins and glycated proteins by measuring the total amount of proteins in the solution to measure after quantifying step.

3. The method of measuring glycated proteins as recited in claim 1,
    wherein the amount of residual labeling compounds is determined by measuring absorbancy, or the amount of fluorescence, phosphorescence or chemiluminescence.

4. The method of measuring glycated proteins as recited in claim 1,
    wherein the labeling compound includes an electrochemical oxidation-reduction pair functional group, a spectroscopic chromophoric group or a substrate functional group of enzyme.

5. The method of measuring glycated proteins as recited in claim 1,
    wherein the labeling compound includes ferrocene derivatives, anthraquinone, quinone and its derivatives, and organic conductive salt.

6. The method of measuring glycated proteins as recited in claim 1, wherein the filtering means comprises protein removal filter.

7. The method of measuring glycated proteins as recited in claim 1, wherein the filtering means comprises immune antibodies capable of a specific binding to the proteins for measuring.

8. The method of measuring glycated,proteins as recited in claim 6, wherein the protein removal filter comprises a cellulose film or a nylon film.

* * * * *